(12) United States Patent
Brantley et al.

(10) Patent No.: US 12,171,939 B2
(45) Date of Patent: Dec. 24, 2024

(54) EMERGENCY-USE RESPIRATORY DEVICE

(71) Applicant: Baylor University, Waco, TX (US)

(72) Inventors: Matthew R. Brantley, China Spring, TX (US); Raymond Curtice, Woodway, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 0 days.

(21) Appl. No.: 18/143,352

(22) Filed: May 4, 2023

(65) Prior Publication Data
US 2023/0355905 A1 Nov. 9, 2023

Related U.S. Application Data

(60) Provisional application No. 63/338,964, filed on May 6, 2022.

(51) Int. Cl.
*A61M 16/00* (2006.01)
*A61M 16/08* (2006.01)
(Continued)

(52) U.S. Cl.
CPC ...... *A61M 16/024* (2017.08); *A61M 16/0057* (2013.01); *A61M 16/026* (2017.08);
(Continued)

(58) Field of Classification Search
CPC .............. A61M 16/00; A61M 16/0057; A61M 16/0066; A61M 16/0084; A61M 16/024; A61M 16/026; A61M 16/0875; A61M 2205/505; A61M 2205/52; A61M 2016/0027
See application file for complete search history.

(56) References Cited

U.S. PATENT DOCUMENTS 5,678,539 A * 10/1997 Schubert ............. A61M 16/024
128/204.21
5,915,380 A 6/1999 Wallace et al.
(Continued)

FOREIGN PATENT DOCUMENTS

| CN | 211884980 U | 11/2020 | |
| CN | 112604113 A | 4/2021 | |
| WO | WO-2022125840 A1 * | 6/2022 | ............. G16H 50/70 |

*Primary Examiner* — Joseph D. Boecker
(74) *Attorney, Agent, or Firm* — NEO IP

(57) ABSTRACT

A portable ventilator device suitable for emergency use, such as cardiac pulmonary resuscitation and well as ventilation in non-cardiac induced medical events. The device is connected to a display screen that receives simple inputs from an operator, including height, weight, or sex of the distressed patient, but does not require input of more complicated variables, such as tidal volume, respiratory rate, inspiratory airflow, or positive end-expiratory pressure. Based on the input height, weight, and/or sex, the device automatically correlates the input values with probably values for tidal volume, respiratory rate, inspiratory airflow, or positive end-expiratory pressure, based previous data point correlations. The device then begins delivering air from a ventilator to the patient based on the estimated, correlated values. While the device utilizes simple inputs, it still capable of operating in multiple modes with both pressure control and volume control.

20 Claims, 10 Drawing Sheets

(51) Int. Cl.
    *A61N 1/39*           (2006.01)
    *G16H 20/40*        (2018.01)
    *G16H 40/60*        (2018.01)

(52) U.S. Cl.
    CPC ......... *G16H 20/40* (2018.01); *A61M 16/0875* (2013.01); *A61M 2205/3334* (2013.01); *A61M 2205/505* (2013.01); *A61M 2205/52* (2013.01); *A61N 1/3904* (2017.08); *G16H 40/60* (2018.01)

(56) References Cited

U.S. PATENT DOCUMENTS

| | | | |
|---|---|---|---|
| 7,980,244 B2 | 7/2011 | Boone et al. | |
| 8,640,700 B2 | 2/2014 | Baker, Jr. | |
| 10,245,437 B2 | 4/2019 | Kantor et al. | |
| 10,980,417 B2 | 4/2021 | Shen | |
| 11,596,753 B2 | 3/2023 | Sherman et al. | |
| 2002/0185127 A1* | 12/2002 | Melker | A61M 16/0051 128/202.22 |
| 2006/0069326 A1* | 3/2006 | Heath | A61H 31/006 601/41 |
| 2007/0000494 A1* | 1/2007 | Banner | A61B 5/0205 128/204.23 |
| 2007/0045152 A1* | 3/2007 | Kwok | A61M 16/00 206/733 |
| 2008/0000477 A1* | 1/2008 | Huster | A61M 11/06 601/149 |
| 2011/0138315 A1* | 6/2011 | Vandine | A61M 16/0443 715/810 |
| 2012/0302910 A1* | 11/2012 | Freeman | G16H 20/40 128/205.13 |
| 2013/0047989 A1* | 2/2013 | Vandine | A61M 16/026 128/204.23 |
| 2016/0051780 A1* | 2/2016 | Sherman | A61M 16/024 128/204.21 |
| 2016/0067434 A1* | 3/2016 | Schwaibold | A61M 16/024 128/204.23 |
| 2016/0193438 A1* | 7/2016 | White | A61M 16/0003 128/204.23 |
| 2017/0128684 A1* | 5/2017 | Sinderby | A61M 16/024 |
| 2017/0266400 A1* | 9/2017 | McCarthy | A61M 16/06 |
| 2017/0325695 A1* | 11/2017 | Freeman | A61B 5/053 |
| 2019/0224434 A1* | 7/2019 | Silver | A61H 31/00 |
| 2019/0344005 A1* | 11/2019 | Larsson | A61M 1/1698 |
| 2020/0000680 A1* | 1/2020 | Silver | A61H 31/00 |
| 2020/0054520 A1* | 2/2020 | Johnson | A61M 16/026 |
| 2020/0345962 A1* | 11/2020 | Hansmann | A61M 16/127 |
| 2021/0187222 A1* | 6/2021 | Dickens | A61M 16/0057 |
| 2021/0330913 A1* | 10/2021 | Martin | A61M 16/107 |
| 2021/0393902 A1* | 12/2021 | Dong | A61M 16/0003 |
| 2021/0402119 A1* | 12/2021 | Bell | A61M 16/205 |
| 2022/0040428 A1 | 2/2022 | Fogarty et al. | |
| 2022/0072321 A1* | 3/2022 | O'Connor | G16H 40/40 |
| 2022/0105288 A1* | 4/2022 | Beck | G16H 40/67 |
| 2022/0293262 A1* | 9/2022 | Beck | G16H 50/00 |
| 2022/0313929 A1* | 10/2022 | Beck | A61M 16/0003 |
| 2023/0131417 A1* | 4/2023 | Scott | A61H 31/007 128/202.22 |

* cited by examiner

EMERGENCY-USE RESPIRATORY DEVICE

CROSS REFERENCE TO RELATED APPLICATIONS

This application is related to and claims priority from the following U.S. patent application. This application claims priority to and the benefit of U.S. Provisional Patent Application No. 63/338,964, filed May 6, 2022, which is incorporated herein by reference in its entirety.

BACKGROUND OF THE INVENTION

1. Field of the Invention

The present invention relates to respiratory devices and methods, and more specifically to portable ventilators having simplified inputs and therefore being capable of being operated by non-medical professionals without prior training.

2. Description of the Related Art

It is generally known in the prior art to provide ventilators for assisting breathing by providing air into a patient's lungs. Both positive pressure ventilators, which push air directly into the lungs, and negative pressure ventilators, which help to allow air to passively be drawn into the lungs, are known in the art. Some positive pressure ventilators only focus on pushing air into the lungs in sync with a patient's breathing, while others, especially invasive mechanical ventilators, take over the breathing process more thoroughly, pushing in air and pulling out carbon dioxide breathed out by the patient.

U.S. Pat. No. 10,245,437 for System and method for providing noninvasive ventilation by inventors Kantor et al., filed Nov. 10, 2013 and issued Oct. 22, 2015, discloses a system that includes both an Airway and Ventilation device (AV) and an Automated External Defibrillator (AED) device. The system allows minimally trained persons to operate it in emergency situations involving respiratory failure and/or cardiac arrhythmias. An integral part of the AV of the system is a face mask manufactured in two parts: a face attachment unit configured to attach to the patient's face and a mask body that is releasably connected to the face attachment unit by a quick release mechanism allowing quick removal of the mask body from the face attachment unit, leaving only the face attachment unit attached to the patients' face, in order to address urgencies such as vomiting. After vomiting ceases and is cleared, then the mask body may be reattached to continue ventilation.

U.S. Pat. No. 7,980,244 for Emergency pulmonary resuscitation device by inventors Boone et al., filed Jul. 17, 2007 and issued Jul. 19, 2011, discloses an emergency pulmonary resuscitation device. The device of the present invention provides emergency breathing for use in techniques such as CPR, and is preferably capable of interaction with an automatic external defibrillator. The device is easy to operate and provides feedback so that it may be used by persons without medical training. The device also works through a simple action, making it possible for it to be inexpensively manufactured and widely disseminated.

U.S. Pat. No. 11,596,753 for Automatic patient ventilator system and method by inventors Sherman et al., filed Nov. 5, 2015 and issued Mar. 7, 2023, discloses ventilator enabling an operator to enter into the microprocessor estimate of a patient's individual characteristic, such as weight, which the microprocessor uses to control delivered tidal volume and other parameters to match the patient. The operator can select one of several ventilator operational modes (intube, mask, CPR). Sensors input data to the microprocessor to maintain parameter optimizations and accuracy. Visual/audible alarms and tools activate when one or more parameters exceed or fail to exceed predetermined values for patient's weight. Manual override is available. The ventilator has a quick start capability in which the operator turns on power, selects the automatic operating mode, enters patient's characteristic, selects control option starting automatic ventilation of proper volumes inhalation/exhalation periods, pressure, and oxy-air mixture.

U.S. Pat. No. 5,915,380 for System and method for controlling the start up of a patient ventilator by inventors Wallace et al., filed Mar. 14, 1997 and issued Jun. 29, 1999, discloses a ventilation control system for controlling the ventilation of a patient. The ventilation control system utilizes a user-friendly user interface for the display of patient data and ventilator status, as well as for entering values for ventilation settings to be used to control the ventilator. Values for ventilation settings entered during set up of the ventilator result in the display of only those further ventilation settings that are appropriate in accordance with the earlier entered settings.

U.S. Patent Pub. No. 2021/0393902 for One-touch ventilation mode by inventors Dong et al., filed Jun. 22, 2021 and published Dec. 23, 2021, discloses systems and methods for one-touch ventilation mode. In examples, settings for a medical ventilator are determined and delivered to a patient with a minimum of one input parameter. The one-touch ventilation mode may reference or apply one or more respiratory mechanics planes to determine desired ventilation parameters. In an example, the input parameter may be mapped to initial ventilation settings on a respiratory mechanics plane. During ventilation delivered according to the initial ventilation settings, ventilation data may be obtained. Based on the ventilation data, one or more ventilation strategies may be implemented, including breath type strategy, alarming strategy, triggering/cycling strategy, and PEEP strategy. Updated ventilation settings may be determined based on the ventilation data and/or the ventilation strategy.

U.S. Pat. No. 8,640,700 for Method for selecting target settings in a medical device by inventor Baker, filed Mar. 23, 2009 and issued Feb. 4, 2014, discloses providing a method for controlling the delivery of a breathing gas to a patient. The method may include regulating the delivery of the breathing gas delivered to the patient, determining a value for a first ventilation parameter, comparing the determined value of the first ventilation parameter to a pre-determined target value for the first ventilation parameter, automatically adjusting the breathing gas delivered to the patient in response to the comparison between the determined value of the first ventilation parameter and the pre-determined target value for the first ventilation parameter, and automatically determining a new target value for the first ventilation parameter based at least in part on the determined value of the first ventilation parameter.

U. S. Patent Pub. No. 2022/0040428 for Ventilation Devices and Systems and Methods of Using Same by inventors Fogarty et al., filed Aug. 18, 2021 and published Feb. 10, 2022, discloses a ventilation system having a mask, a blowing assembly, and a processor. The mask has a mask body and a pressure sensor operatively associated with the mask body and configured to measure pressure within the mask. The mask body defines an inlet opening and a plurality of leak openings. The blowing assembly is positioned in fluid communication with the inlet opening of the mask body and configured to direct air to the inlet opening of the mask body. The processor is positioned in operative communication with the blowing assembly and the pressure sensor of the mask. The processor is configured to selectively control the blowing assembly based upon at least the measured pressure within the mask.

U.S. Pat. No. 10,980,417 for Acute care eco system integrating customized devices of personalized care with networked population based management by inventor Shen, filed May 12, 2015 and issued Apr. 20, 2021, discloses a personalized acute care treatment kit that includes components necessary for a lay caregiver to treat an acute cardiac event. The kit includes a medication box provided with medications selected according to the needs of the owner, a CPR device, a pacemaker, a defibrillator, monitoring and diagnostic devices and a computing device. The computing device is provided with a mobile application that captures patient data from the devices in the kit and automatically sends an alarm to a treatment professional when the patient data exceeds a predetermined threshold and establishes a communication link to with the treatment professional to allow the treatment professional to instruct the lay caregiver in using the contents of the kit to provide acute care.

SUMMARY OF THE INVENTION

The present invention relates to respiratory devices and methods, and more specifically to portable ventilators having simplified inputs and therefore being capable of being operated by non-medical professionals without prior training.

It is an object of this invention to provide an easy-to-use display interface for a portable ventilator accepting simplified input parameters for a patient that are able to be understood by non-medical users, such as height, weight, and sex, so as to provide temporary, emergency ventilation until medical professionals are able to arrive.

In one embodiment, the present invention is directed to a portable emergency ventilator system, including a controller, a mechanical ventilator connected to tubing operable to supply air to at least one patient, wherein the controller is in communication with at least one user input device, wherein the at least one user input device receives input values corresponding to a height, a weight, and/or a sex of the at least one patient, wherein the received input values do not include tidal volume, positive end-expiratory pressure, respiratory rate, or inspiratory airflow of the at least one patient, and wherein the controller automatically controls the volume and/or pressure of air delivered by the mechanical ventilator to the at least one patient based on the received input values.

In another embodiment, the present invention is directed to a portable emergency ventilator system, including a casing containing a controller and a mechanical ventilator, wherein the mechanical ventilator is connected to tubing operable to supply air to at least one patient, wherein the controller is in communication with at least one user input device, wherein the at least one user input device receives input values corresponding to a height, a weight, and/or a sex of the at least one patient, wherein the controller automatically controls the volume and/or pressure of air delivered by the mechanical ventilator to the at least one patient based on the received input values, wherein the casing includes at least one recession shaped to hold the tubing, and wherein the casing is attached to at least one flap, where the flap is configured to cover the recession in the casing in a closed position.

In yet another embodiment, the present invention is directed to a portable emergency ventilator system, including a controller, a mechanical ventilator connected to tubing operable to supply air to at least one patient, wherein the controller is in communication with at least one user input device, wherein the at least one user input device receives input values corresponding to a height, a weight, and a sex of the at least one patient, wherein the controller is connected to a memory and/or in communication with a database, and wherein the memory and/or the database include a plurality of data point correlations between a first group of quantities including height, weight, and/or sex and a second group of quantities, including tidal volume, positive end-expiratory pressure, respiratory rate, and/or inspiratory airflow, wherein the controller automatically generates estimated values for the tidal volume, the positive end-expiratory pressure, the respiratory rate, and/or the inspiratory airflow of the at least one patient based on the input values and the plurality of data point correlations in the memory and/or the database, and wherein the controller automatically controls the volume and/or pressure of air delivered by the mechanical ventilator to the at least one patient based on the estimated values.

DETAILED DESCRIPTION

Figure 1:
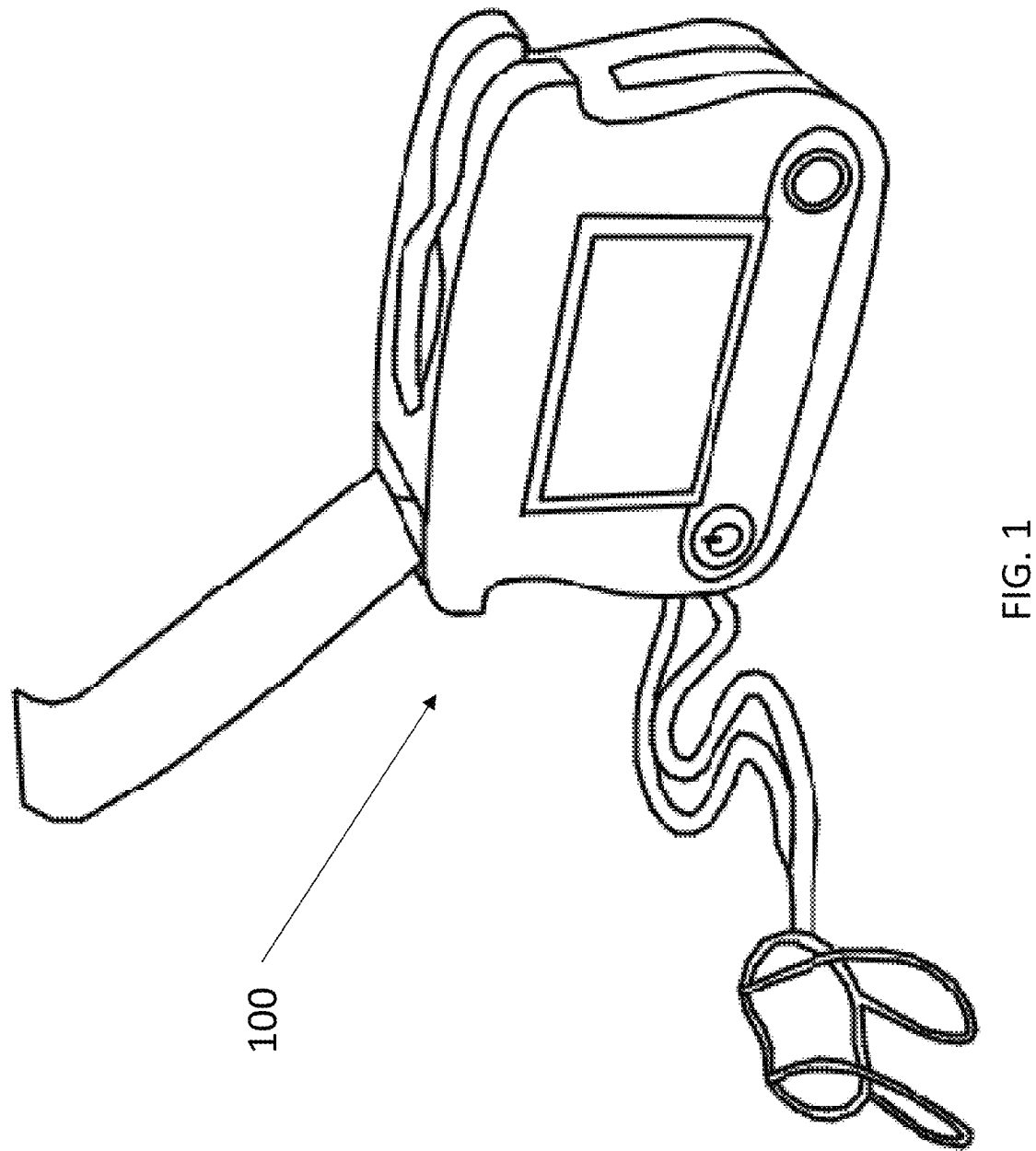
FIG. 1 is a perspective view of a portable ventilator according to one embodiment of the present invention.

The present invention relates to respiratory devices and methods, and more specifically to portable ventilators having simplified inputs and therefore being capable of being operated by non-medical professionals without prior training.

In one embodiment, the present invention is directed to a portable emergency ventilator system, including a controller, a mechanical ventilator connected to tubing operable to supply air to at least one patient, wherein the controller is in communication with at least one user input device, wherein the at least one user input device receives input values corresponding to a height, a weight, and/or a sex of the at least one patient, wherein the received input values do not include tidal volume, positive end-expiratory pressure, respiratory rate, or inspiratory airflow of the at least one patient, and wherein the controller automatically controls the volume and/or pressure of air delivered by the mechanical ventilator to the at least one patient based on the received input values.

In another embodiment, the present invention is directed to a portable emergency ventilator system, including a casing containing a controller and a mechanical ventilator, wherein the mechanical ventilator is connected to tubing operable to supply air to at least one patient, wherein the controller is in communication with at least one user input device, wherein the at least one user input device receives input values corresponding to a height, a weight, and/or a sex of the at least one patient, wherein the controller automatically controls the volume and/or pressure of air delivered by the mechanical ventilator to the at least one patient based on the received input values, wherein the casing includes at least one recession shaped to hold the tubing, and wherein the casing is attached to at least one flap, where the flap is configured to cover the recession in the casing in a closed position.

In yet another embodiment, the present invention is directed to a portable emergency ventilator system, including a controller, a mechanical ventilator connected to tubing operable to supply air to at least one patient, wherein the controller is in communication with at least one user input device, wherein the at least one user input device receives input values corresponding to a height, a weight, and a sex of the at least one patient, wherein the controller is connected to a memory and/or in communication with a database, and wherein the memory and/or the database include a plurality of data point correlations between a first group of quantities including height, weight, and/or sex and a second group of quantities, including tidal volume, positive end-expiratory pressure, respiratory rate, and/or inspiratory airflow, wherein the controller automatically generates estimated values for the tidal volume, the positive end-expiratory pressure, the respiratory rate, and/or the inspiratory airflow of the at least one patient based on the input values and the plurality of data point correlations in the memory and/or the database, and wherein the controller automatically controls the volume and/or pressure of air delivered by the mechanical ventilator to the at least one patient based on the estimated values.

The pandemic of SARS-CoV-2, commonly known as COVID-19, taught the public the necessity of respiratory devices, such as ventilators. During the COVID-19 pandemic, hospitals and medical staff frequently needed more ventilators than were available. The needs are even more acute outside the medical centers, such as hospitals and urgent care facilities, where untrained users are called upon to render aid, particularly in emergencies. The last few years found untold millions of people needing respiratory aid outside of the medical centers at least temporarily until medical help is able to be present. The expense of a ventilator discouraged businesses from having such a device on premises and often precluded a homeowner from purchasing one. Further, the complexity of skillfully operating such a sophisticated ventilator to provide sufficient air, yet correctly to avoid harming the patient dissuades many from operating such devices.

Further, a patient's emergency need for ventilation is often a highly stressful event with family members, friends, and coworkers. Logic and deliberation are often compromised. Attempting to operate a sophisticated ventilator that is able to provide the needed air sometimes causes harm to the patient. While some simple devices are commercially sold for ventilation, such known systems lack the ability to handle the varying needs of patient to adequately provide the air without harming the patient that needs the air that the more sophisticated devices in medical centers operated by trained medical personnel are able to provide.

Different ventilators operate in vastly different ways, both in terms of which mechanical circuit elements are included and what operating modes are used to run them. With regard to mechanical configuration, ventilators, particularly those with a dual limb configuration, frequently include a Y-piece connected to both an inhalation tube and an exhalation tube. The inhalation tube is sometimes attachable to a temperature sensor for detecting the incoming air temperature, such that a feedback loop is able to be formed. Ventilators commonly include a heat and moisture exchanger (HME) for humidifying incoming air and, occasionally, the temperature sensor is placed where the air exits the humidifier. Some ventilation circuits also include heated wires running the length of the tubing in order to maintain a consistent temperature. The inhalation tube or the Y-piece also sometimes includes a port for administering nebulized drugs. Often ventilator circuits will also include filters both for incoming air and for exhaled gas. Sometimes, filters are included both where the inhalation tubing and exhalation tubing are attached to the ventilator, with an additional filter attached to the Y-component for increased safety. Inspiratory filters help to prevent patient infection from a potentially infected ventilator, while expiratory filters help to protect the device and the surrounding healthcare staff from contamination from the patient. Sometimes, inspiratory filters are combined with the HME and placed proximate to the Y-piece.

Single limb ventilators are an alternative to dual limb ventilators and do not include distinct inhalation and exhalation pathways. Instead, single limb set ups utilize exhaust valves to externally remove exhaled air, rather than a distinct exhalation pathway back to the ventilator.

Systems for compressing air to generate a positive pressure for ventilators include bellows generators, which use a driving gas to pressurize a bellows to compress the air, and piston ventilators, which utilize an electronic motor to drive compression of a piston within a chamber to compress the gas. Generally, piston ventilators are preferred, given the more precise control over tidal volumes and the potential harmful leakage of the driving gas used in bellows ventilators (especially descending bellows ventilators), among other reasons. One alternative to the pressure solutions of both bellows and piston ventilators is a turbine-based ventilator, which is able to take in air through a turbine to deliver high amounts of that air to support ventilator operations.

Ventilators typically operate using control of volume, pressure, or both, but each of these modes often require precise monitoring from medical professionals to ensure the safety of the patient. A ventilator using pressure control (i.e., configured to deliver a set amount of pressure) is often advantageous, as it allows the device to be operated without risk of barotrauma or other injuries caused by overinflation of the lungs. However, pressure control does not account for an obstruction to inhaling the air from the ventilator, causing the amount of delivered pressure to be insufficient to flow of needed air does not flow into the lungs, resulting in possible morbidity without careful supervision. On the other hand, ventilators utilizing volume control typically are advantageous as they allow operators to set amounts of volume based on monitoring the patient's condition, helping to more precisely reach a desired value of PaCO2. However, left unattended, volume control fails to account for an inability to exhale properly the incoming air, resulting in a buildup of air in the lungs and overpressure, leading to barotrauma or even bursting of the lungs.

Once the control variable (either volume or pressure) is set, then the operating mode is able to be set. The two primary operating modes are assist/control (A/C) and synchronous intermittent mandatory ventilation (SIMV). A/C typically delivers a preset number of mandatory breaths, but allows the patient to also trigger their own breaths. Even if the patient triggers their own breaths, A/C allows the ventilator to entirely deliver the breaths. A/C is good in ensuring that patients utilize less effort to deliver each breath, as the machine does the work, but carries the risk of triggering hyperventilation, which is sometimes lethal. SIMV also allows delivers a preset number of mandatory breaths, but also allows the patient to initiate spontaneous breaths between mandatory breaths. SIMV is able to be run with either pressure control or volume control. SIMV allows patients to contribute more to the breathing, as they are able to initiate the spontaneous breaths and is therefore useful for weaning a patient off support. SIMV helps to maintain respiratory muscles, distributes even tidal breaths, and decreases mean airway pressure. However, other spontaneous modes (relying on spontaneous breaths from patients) are also used, including continuous positive airway pressure (CPAP), pressure support ventilation (PSV), and volume support (VS). Some additional, secondary modes include and/or control mode ventilation (CMV), airway pressure release ventilation (APRV), mandatory minute ventilation (MMV), inverse ratio ventilation (IRV), pressure-regulated volume control (PRVC), proportional assist ventilation (PAV), adaptive support ventilation (ASV), adaptive pressure control (APC), volume-assisted pressure support (VAPS), neurally adjusted ventilatory assist (NAVA), automatic tube compensation (ATC), and/or high frequency oscillatory ventilation (HFOV).

While the range of these modes and the ability of some ventilators to select from different modes is helpful for allowing doctors or other medical professionals to adapt very particularized long-term care to patients based on patient specific conditions, the difficulty of operating ventilator devices keeps them from being able to be operated by an average, non-licensed medical professional. For example, the input variables for ventilators typically at least include tidal volume ($V_T$), positive end-expiratory pressure (PEEP), respiratory rate (RR), and inspiratory airflow (V'). However, the average individual is incapable of understanding how to measure these variables or what they signify. Therefore, a non-trained individual attempting to operate a prior art ventilator is at high risk of injuring the patient being ventilated, perhaps even severely.

Therefore, there is a need for a ventilator that is able to operate sophisticated modes suitable for medically trained personnel, yet enable a user without medical training to operate when respiratory relief is needed, even in emergency situations apart from medical centers. Such a device is preferably able to serve as a complementary device to an automated external defibrillator (AED) in allowing average people to use complex, dangerous medical equipment in emergency situations with low risks of harm.

The present disclosure provides a ventilator suitable for emergency use, such as cardiac pulmonary resuscitation as well as ventilation in non-cardiac induced medical events. The device operates in a mode that allows sophisticated performance with optionally multiple inputs that are used to automatically control the ventilator operation by an onboard controller. The ventilator is able to operate in various modes that are more customary to medically trained personnel, or a combination thereof.

The present system is particularly useful in an emergency situation, particularly within the first eight minutes of a respiratory event, before paramedics are able to arrive. The system functions to provide oxygen to the patient during this time, helping prevent hypoxia, and helps remove CO2 from the patient's body, preventing respiratory acidosis that causes tissue or organ damage. In this way, the system is particularly useful as an at-home unit, a travel appliance, a commercial unit, and/or a disaster response tool, as all of these situations require quick and nimble deployment in the field, where hospital-level resources are not available. Additionally, because the present system utilizes simplified pictorial instructions, it is capable of being operated by a large number of people, literate in a wide variety of languages.

FIG. 1 is an illustrative example of an embodiment of the ventilator that is able to be used, for example, in conjunction with an AED device. The ventilator 100 generally departs from a hospital ventilator in terms of both size and complexity. The ventilator 100 has the capability to perform at a sophisticated level, comparable to that of a hospital ventilator, but avoids complexities in operation in at least some embodiments by a user-friendly interface that requires limited input in order to operate on a less sophisticated level. Based on several simple, easy-to-understand inputs, a non-medical user with minimal training is able to use the ventilator 100, especially in cases of respiratory emergencies. In at least one embodiment, the respirator device is in a form suitable for use with an automated external defibrillator ("AED") device commonly used for cardiac pulmonary resuscitation ("CPR"). In another embodiment, the respirator is combined with an AED as a single device. In one embodiment, the ventilator 100 is mounted in a cabinet adjacent the AED cabinet for easy access as needed.

Generally, a two-person CPR procedure is recommended having one person to push on a patient's chest to manually pump the patient's heart, while another person breathes air into the patient's lungs to help ventilate the patient for an interim period. The ventilator 100 substitutes for the person respirating the patient, allowing one person to perform the CPR without also having to manually ventilate. In this situation, the ventilator is used in a resuscitator capacity. In one use case example, a patient needs additional air support in their lungs due to a sudden injury, disease, or a chronic condition, which the ventilator 100 is able to provide.

Figure 2:
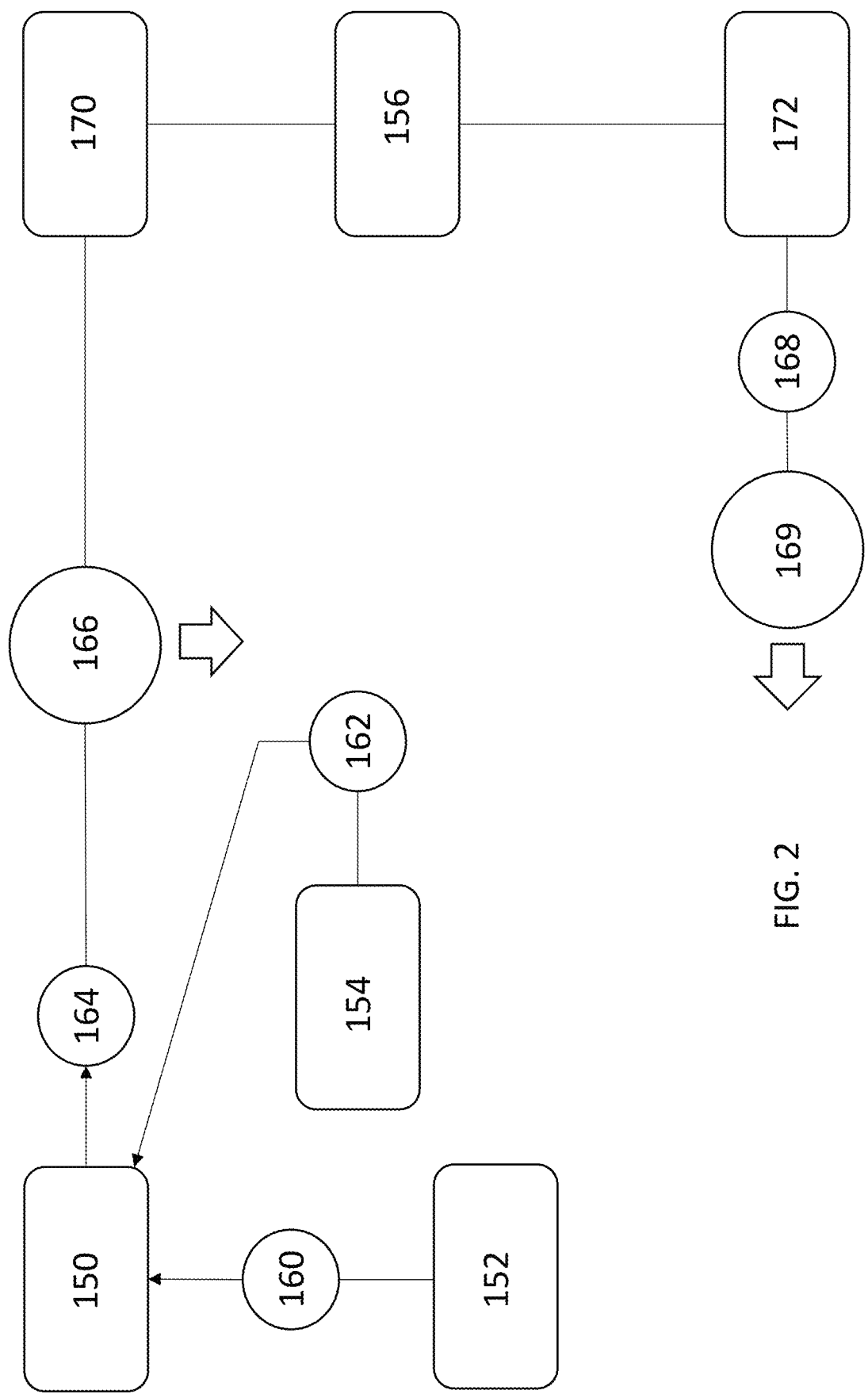
FIG. 2 is a schematic diagram of mechanical components of a portable ventilator according to one embodiment of the present invention.

FIG. 2 is a schematic diagram of components of an embodiment of the ventilator system. The ventilator system includes a series of components with a controller that manages the several inputs and provide outputs to the components in various modes. In one embodiment, the ventilator includes, by way of example and not limitation, a ventilator 150 connected to an air supply 152 and/or a supplemental oxygen supply 154, such that the ventilator 150 is able to mix air and supplemental oxygen to deliver to a patient. In one embodiment, the air supply 152 is connected to the ventilator 150 via at least one valve 160 (e.g., a solenoid valve). In one embodiment, the at least one valve 160 includes an ambient air valve, able to control an amount of air that is able to enter a suction port of the ventilator 150. In one embodiment, the system includes at least one air quality sensor operable to detect an air quality entering the ventilator. In one embodiment, the supplemental oxygen supply 154 is connected to the ventilator via at least one valve 162 (e.g., a solenoid valve). Air from the ventilator 150 is transported through tubing to a patient 156. In one embodiment, air from the ventilator 150 passes through at least one valve 164 (e.g., a solenoid valve) before reaching the patient, allowing the at least one valve 164 to regulate the ventilator output. One of ordinary skill in the art will understand that while the supplemental oxygen supply 154 is able to be included in the present invention, it is not necessary in order to operate and the system is capable of using air alone. In one embodiment, the system includes at least one oxygen concentrator in order to increase the percentage of oxygen in the delivered air without providing a supplemental oxygen canister. In one embodiment, the ventilator system includes one or more ampoules of an oxygenating compound. In one embodiment, if the ventilator system detects low oxygen in the inspiratory line, then a preset quantity of the oxygenating compounds is automatically added to the inspiratory line such that they are able to be delivered to the patient.

One of ordinary skill in the art will understand that the ventilator system is not limited to only single limb or dual limb embodiments. In one embodiment, for a single limb design, exhaled gas is released through an exhalation valve. In another embodiment, for a dual limb design, exhaled gas is returned through an exhalation circuit through a first valve 168 (e.g., a solenoid valve). In one embodiment, the exhalation circuit includes at least one positive end-expiratory pressure (PEEP) valve 169, which allows the controller to maintain a pressure in the exhalation pathway greater than atmospheric pressure. In one embodiment, the inhalation line of the circuit includes at least one pressure relief valve 166, able to release an amount of air from the line to reduce the inspiratory pressure of the system, if needed. In one embodiment, the ventilation circuit includes at least one heat and moisture exchanger (HME) for managing temperature and/or humidity of the incoming air. In one embodiment, the inspiratory limb of the system includes at least one heated wire disposed within the tubing that is able to be resistively heated, providing consistent temperature of air to the patient. However, one of ordinary skill in the art will understand that the system is capable of operating without any HMEs or heated wires, as the present invention is intended, most importantly, for short time where temperature and humidity are less critical in comparison to long-term care.

In one embodiment, the system includes at least one inspiratory pressure sensor 170 operable to detect the pressure of the air along the inspiratory pathway of the ventilation circuit and/or at least one exhalation pressure sensor 172 positioned along an exhalation pathway of the ventilation circuit. Data from the at least one inspiratory pressure sensor 170 and/or the at least one exhalation pressure sensor 172 is transmitted to a controller of the ventilation system, and is able to be used to provide feedback for the tidal volume or pressure needed to be delivered by the ventilator 150. In one embodiment, the at least one inspiratory pressure sensor 170 and/or the at least one exhalation pressure sensor 172 are replaced or supplemented with flow rate sensors, operable to detect a flow rate of air entering the patient 156 or gas being exhaled from the patient 156. In one embodiment, flow rate sensors and/or pressure sensors, especially on the inspiratory side, are able to be used to detect when a patient is inhaling or attempting to inhale and send feedback to the controller to modulate the output of the ventilator 150 or the flow allowed by the at least one valve 164 in order to aid the breathing process of the patient 156. In one embodiment, based on parameters of the patient (e.g., height, sex, and/or weight), the system automatically sets a maximum pressure, a minimum pressure, a maximum flow rate, and/or a minimum flow rate for operation. If the pressure sensors or flow rate sensors detect that the system is operating outside of those parameters, the system is operable to automatically change operation of the ventilator (e.g., increase pressure, increase flow rate, decrease pressure, etc.).

In one embodiment, the ventilation includes at least one oxygen sensor and/or at least one carbon dioxide ($CO_2$) sensor. In one embodiment, the at least one oxygen sensor is attached to the inspiratory limb of the ventilation circuit and is able to generate and transmit and $O_2$ concentration of the inspiratory air, such that the controller is able to, for example, control the relative contribution of at least one supplemental oxygen supply to the inspiratory air supply. In one embodiment, the ventilation system is able to be fitted with an external oxygen supply system. This is useful in the event that the ventilator is used in a hospital setting (e.g., after a patient is brought in from using it in the field), as it allows the ventilator to operate with additional equipment to deliver care to the patient. In one embodiment, the at least one $CO_2$ sensor is attached to an expiratory limb of the ventilation system. In one embodiment, the at least one $CO_2$ sensor detects the presence, but not necessarily the concentration, of $CO_2$ in the exhalation pathway to ensure that the patient is actually being assisted in breathing, rather than simply pumping air into the patient that then passes out.

One of ordinary skill in the art will understand that filters (such as bacterial and viral filters) are able to be positioned along various points of the ventilation circuit. By way of example and not limitation, filters are able to be replaced at a position in the ventilation circuit where air leaves the ventilator 150 and/or at a position proximate to where air to delivered to the patient 156 (e.g., connected to a Y-piece). Filters along the inspiratory pathway help to prevent contaminating the patient in the event that the ventilator itself is contaminated. In one embodiment, at least one filter is placed at a position along an exhalation path within the ventilation circuit, which helps to prevent contamination of the ventilator 150 in the event that the patient 156 is sick. In another embodiment, the system does not include any filters.

One of ordinary skill in the art will understand that the mechanism of the ventilator according to the present invention is not intended to be limiting. In a preferred embodiment, the system includes a turbine-based ventilator system. However, in other embodiments, the system includes a piston ventilator, a bellows ventilator, and/or any other type of ventilator.

A display device coupled to the controller accepts input parameters, requests information and displays results and/or a status of the patient. As an example of a typical form of control in hospital respirator devices, a controller includes a first control method correspond to a volume control that controls a volume of inspiratory air delivered to a patient, but does not directly control pressure. Another typical control method is a pressure control method that controls the pressure of inspiratory air, but does not directly control volume.

In one embodiment, most of the elements of the system, including the ventilator, the controller, and the display, are contained within a casing, as shown with the device in FIG. 1. An exception is the tubing for connecting to the patient, as this tubing needs to extend some length and there cannot always be contained within the casing. However, in one embodiment, when the device is not in use, the tubing is able to be collapsed and fit within an internal recess of the casing. In one embodiment, the casing also includes at least one power source (e.g., at least one battery, at least one solar cell, etc.) for powering operations of the ventilator even when not connected to an outlet. In one embodiment, the casing includes at least one port for connecting to an electrical outlet. One of ordinary skill in the art will understand that the type of power port used for the ventilator is able to vary and nothing in the present invention is intended to be limiting in that regard.

In one embodiment, the casing includes at least one geolocation sensor (e.g., at least one Global Positioning System (GPS) chip). In one embodiment, the at least one geolocation sensor is integrated with at least one cellular card. In one embodiment, the casing includes at least one wireless module operable to communicate data from the ventilator system over a network (e.g., via cellular connection, via a wireless local area network (WLAN), via a wireless personal area network (WPAN), via satellite communications, etc.) to a central server and/or to one or more specific recipients. In one embodiment, when the ventilation system is activated, the casing automatically transmits a signal to a nearby hospital or medical office including the geolocation data, such that medical professionals are able to locate and assist the patient in distress. In one embodiment, the ventilation system is able to pair with at least one external user device (e.g., a cellular phone, a laptop, a tablet, etc.) and automatically transmits the geolocation and/or other sensor data from the casing to the external user device. The external user device is then able to use a software application to select at least one nearby medical office or hospital and automatically transmits data from the ventilation system to the medical office or hospital, allowing the medical professionals to be informed about a real time status and location of the patient. In one embodiment, the ventilation system includes at least one speaker operable to play at least one emergency beacon sound. By playing this loud noise, medical professionals are able to locate the patient after arriving in the geolocated position, which is especially useful if the area is crowded.

In one embodiment, the controller automatically determines initial operating parameters for the ventilation system based on simple patient characteristics input through an associated input device (e.g., an attached display, a cell phone, a computer, a tablet, etc.). In one embodiment, the initial operating parameters include tidal volume, respiratory rate, and/or pressure. In one embodiment, the respiratory rate is preset between approximately 10 and 12 breaths per minute. In one embodiment, in order to determine the initial operating parameters, the controller utilizes at least one table having corresponding values for tidal volume, respiratory rate, and/or pressure for each input height and/or for each combination of height with other characteristics (e.g., sex, weight, etc.). In one embodiment, the initial operating parameters include maximum pressure, minimum pressure, maximum air flow, and/or minimum air flow for the sensors. In one embodiment, the controller is operable to automatically change at least some of the operating parameters (e.g., tidal volume, pressure, etc.) based on readings on inspiratory or expiratory pressure or flow rate sensors detecting pressures or flow rates outside of the tolerable range for the particular patient. In this way, the system is able to be responsive to a patient's current condition, rather than overpressurize or under supply the patient's lungs. In another embodiment, the controller includes at least one artificial intelligence module operable to automatically determine the initial operating parameters and/or to change the operating parameters during use.

In one embodiment, upon activation of the ventilation system, the ventilation system automatically attempts to connect to at least one network (e.g., a cellular network, a WLAN network, a WPAN network, a satellite network, etc.) and automatically retrieves and provides updated data from a cloud serving, adjusting operation of the ventilation system. By way of example and not limitation, if new research indicates it is optimal to provide mandatory breaths at respiration rates between 8-9 breaths per minute, rather than 10-12 breaths per minute, then the ventilation system is updated to automatically provide 8-9 breaths per minute (when in a mode having mandatory breaths). Additionally, if new patient data indicates different optimal tidal volumes or pressures for patients of a given height, then the tables utilized by the controller are able to be automatically updated to reflect this new data.

In one embodiment, the device begins operating in a spontaneous operation mode, such that it detects attempted breaths based on negative pressure readings and then is able to supplement those breaths. In this embodiment, the device does not begin by providing mandatory breaths, but only works as a supplemental tool. In one embodiment, the spontaneous operation mode includes pressure support ventilation (PSV). In one embodiment, if the device does not detect any spontaneous breaths for a preset amount of time (e.g., 10 seconds), then the device automatically switches to providing mandatory breaths in a new control mode. In one embodiment, the new control mode includes an assist control (A/C) or synchronized intermittent mandatory ventilation (SIMV) mode, but one of ordinary skill in the art will understand that the system is not limited to those modes. In one embodiment, if the system detects a preset number of spontaneous breaths and/or a preset threshold frequency of spontaneous breaths, then the system automatically switches back to a spontaneous operation mode. One of ordinary skill in the art will understand, however, that the present system is not limited to beginning in a spontaneous mode and, in another embodiment, begins in a non-spontaneous control mode where a set number of mandatory breaths are delivered. The ability of the system to respond to differences in flow rate and pressure allows the system to act entirely autonomously, without the need for an untrained user to manually adjust the settings over time.

The user interface provides a user-friendly experience to an untrained or minimally trained user. For the purposes of this application, minimally trained will be understood to encompass those individuals having basic life support (BLS) training and/or advanced cardiovascular life support (ACLS) training, but not having further formal medical education. The respirator device includes, as referenced above, pictogram instructions, simplified terminology in common parlance, universal signs, color, sound, lights that activate for different steps or functions, voice instructions, and other methods of communicating procedures, requests for information, status, and results. Such features and methods of interaction allow use in various environments including homes, schools, businesses for untrained or minimally trained users, as well as use with more highly trained medical personnel.

As an example of operational input, the ventilator prompts for a patient's height. A database, such as a look-up table or a formula for direct calculation or other correlation of input to ventilator settings, is used to determine appropriate volume at some pressure for a starting point in inspiration. As the ventilator operates, sensor feedback adjusts the volume and/or pressure as needed for an end result that is beneficial with the system operating in an automatic operation. As discussed above, if the system has choices of simulated modes, then the relevant parameter(s) are adjusted only, unless for example, other parameters fall outside of a safety zone to cause the system to override the settings of the selected parameters.

For more accuracy, the ventilator requests one or more additional characteristics of the patient, including weight, sex, any known current condition, such as a current cardiac arrest and other current status, and even past known relevant medical history. The patient inputs are correlated to ventilator parameters for at least initial start of operation.

FIGS. 3-9 are exemplary user interface screens in at least one embodiment for simplified operation by untrained or minimally trained users that allow the exemplary ventilator to function in a sophisticated manner. One of ordinary skill in the art will understand that the user interface screens shown are only illustrative and are able to be selectively offered, modified, or not offered in various embodiments, and that the inputs shown entered into each screen are able to be made optional in some embodiments of the present invention.

Figure 3:
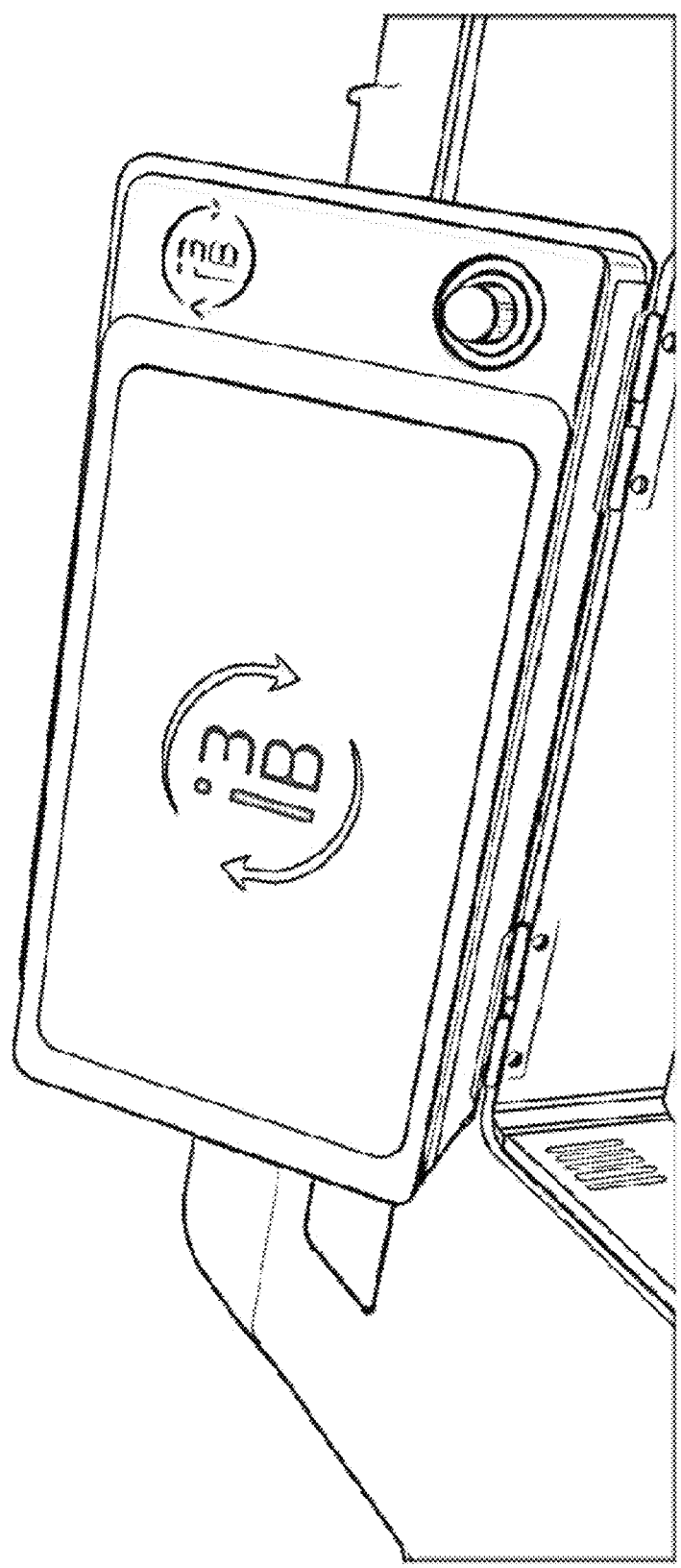
FIG. 3 is a perspective view of a display and input interface of a portable ventilator showing a start-up screen according to one embodiment of the present invention.

FIG. 3 is an illustrative startup screen. The activity on the screen, with FIG. 3 showing rotation of arrows around a central logo, indicates to the user the system is operational and starting up. In one embodiment, the startup screen includes an indication of whether the system is able to access a network, including whether an emergency signal was successfully transmitted to at least one medical professional. In this way, if the startup screen indicates that such a signal failed to go through, then the operator knows that alternate methods need to be used to contact medical professionals.

Figure 4:
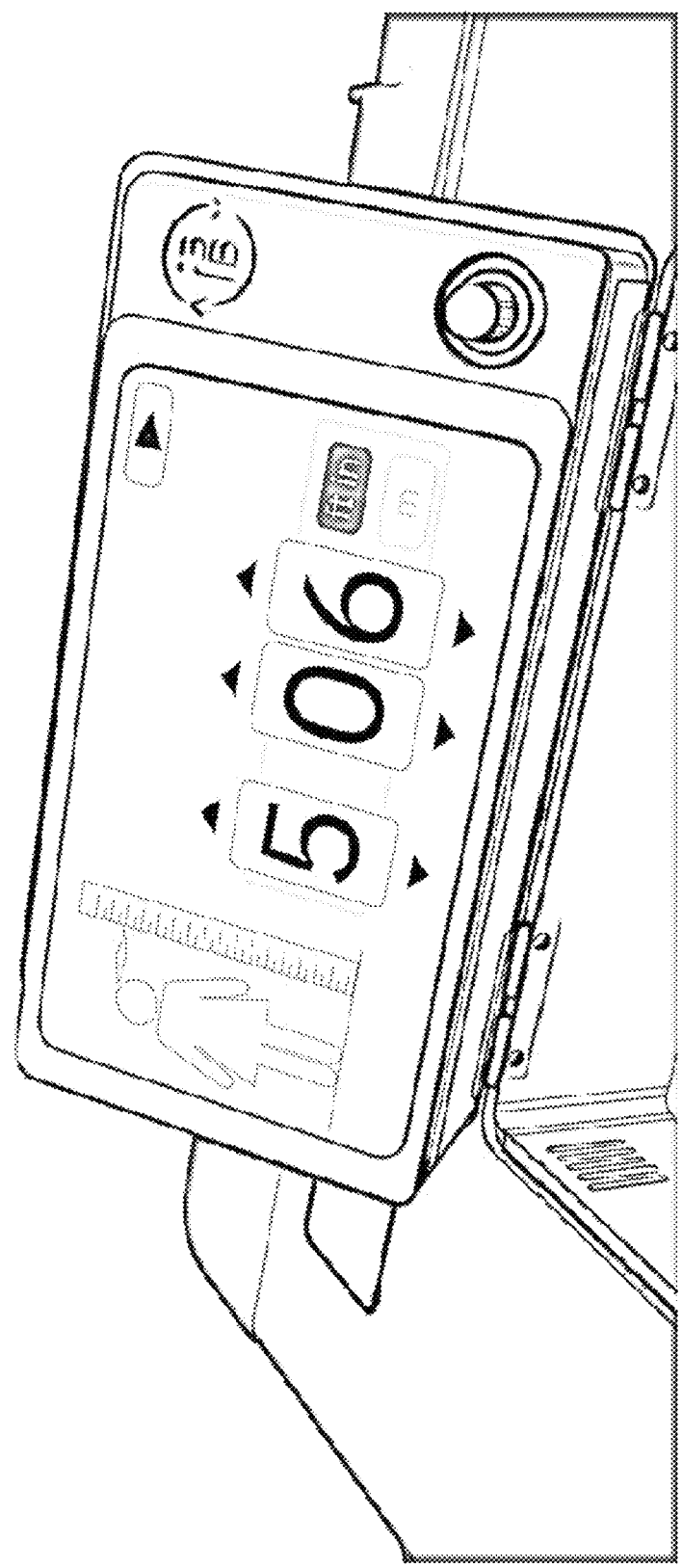
FIG. 4 is a perspective view of a display and input interface of a portable ventilator showing a height input interface according to one embodiment of the present invention.

FIG. 4 is an illustrative user interface screen for height input. In one embodiment, the respirator device operates on the basis of a patient's height using statistical data for selecting estimated respiratory parameters for at least an initial regimen. An advantage of using height as a parameter is that it is easily estimated even by a user with little medical knowledge or other knowledge of the patient, even compared to other visual characteristics, such as weight. In one embodiment, as shown in FIG. 4, height is selected by selecting arrow key buttons that increment or decrement values up and down by one. In one embodiment, the screen is able to receive a selection to change units between metric and imperial units (or other length unit systems), allowing users from different backgrounds to use the system. In one embodiment, height is selected with a slider interface, with a shortest height (or zero) on the left and a tallest height (say, 10 feet) on the right. By moving the slider between these values, the user is able to select a height that matches the patient. In one embodiment, as the slider moves, a pictorial graphic of a user on the screen changes in height, providing more visual feedback for operation of the slider. In one embodiment, the casing of the device includes at least one measuring tape operable to extend out of the casing such that the patient is able to be measured in real time if the operator feels uncertain about their intuitive measurement.

Figure 5:
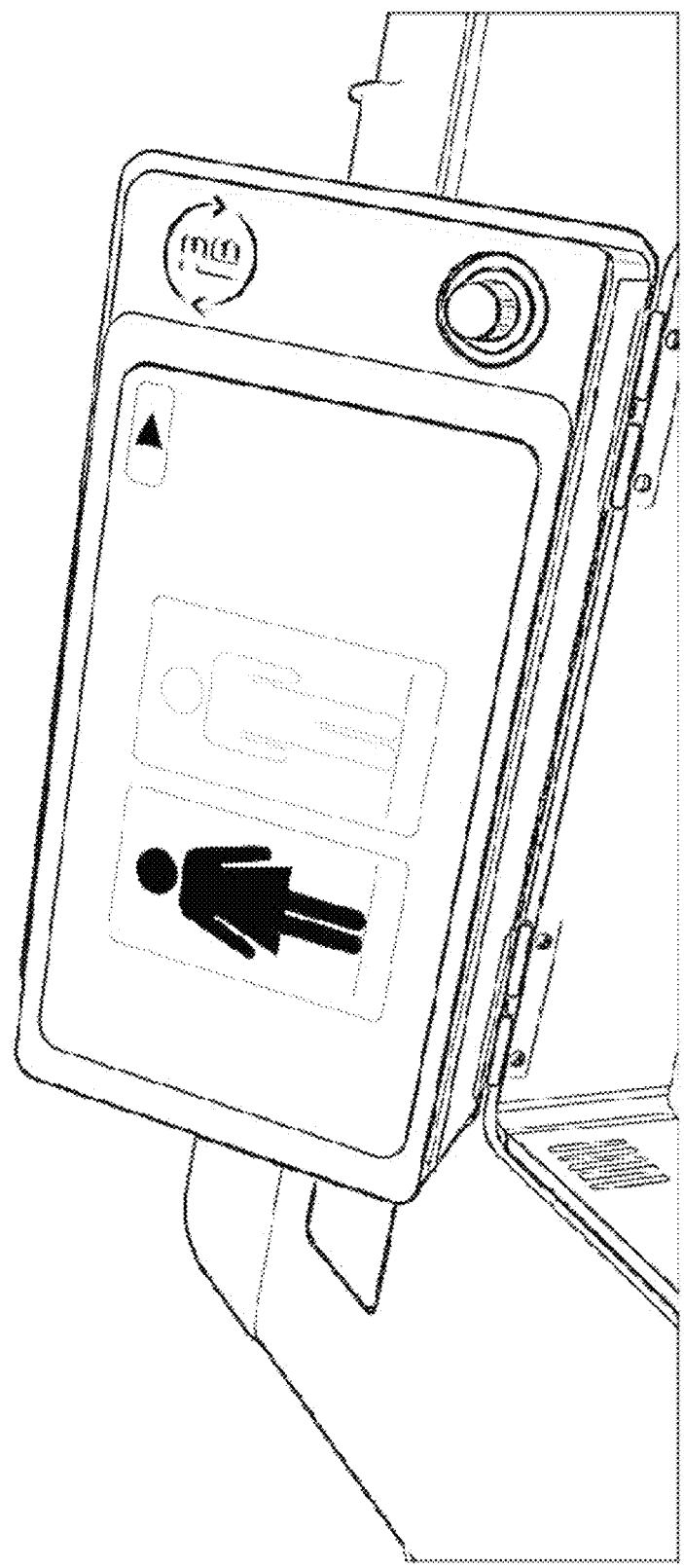
FIG. 5 is a perspective view of a display and input interface of a portable ventilator showing a sex input interface according to one embodiment of the present invention.

FIG. 5 is an illustrative user interface screen for sex input. In lieu of or in addition to height, the patient sex provides some operating parameters for at least an initial setting of the respirator device that the controller is then able to tune, if appropriate, based on results from sensor readings and particularly the patient's inspiratory and expiratory readings as applicable.

Figure 6:
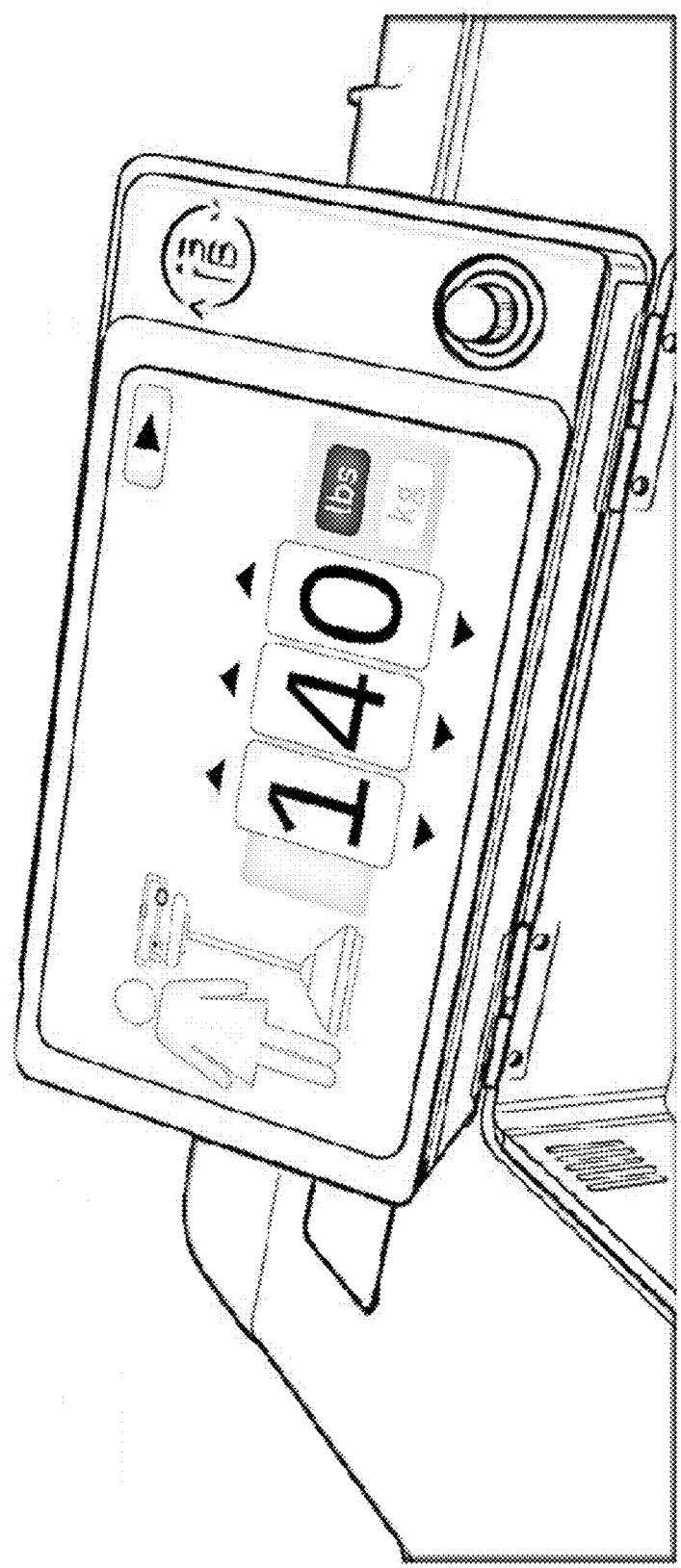
FIG. 6 is a perspective view of a display and input interface of a portable ventilator showing a weight input interface according to one embodiment of the present invention.

FIG. 6 is an illustrative weight input interface. The weight is estimated or actually determined if the patient is conscious and knows their weight or is able to stand on a weight scale. One of ordinary skill in the art will understand that weight is not necessary to include if both height and sex are input, but that in conjunction with the height and/or sex selections, weight sometimes helps to refine the operating parameters. In one embodiment, the weight input interface is able to receive a selection to switch between metric and imperial units of measurement. In one embodiment, weight is selected with a slider interface, with a smallest weight (or zero) on the left and a largest weight (say, 1000 lbs., 50 kg, etc.) on the right. By moving the slider between these values, the user is able to select a weight that matches the patient. In one embodiment, as the slider moves, a pictorial graphic of a user on the screen changes in size, providing more visual feedback for operation of the slider.

In one embodiment, the system further includes an age input interface. The age is estimated or actually determined if the patient is conscious and knows their age or has an ID that indicates their date of birth. One of ordinary skill in the art will understand that age is not necessary to include in the event that both height and sex are input, but that in conjunction with the height and/or sex selections, age sometimes helps to refine the operating parameters. In one embodiment, age is selected with a slider interface, with a youngest age (or zero) on the left and a largest age (say, 115 years) on the right. By moving the slider between these values, the user is able to select an age that matches the patient. In one embodiment, as the slider moves, a pictorial graphic of a user on the screen appears to age, providing more visual feedback for operation of the slider. In one embodiment, if an age is selected that falls outside of the acceptable range of use for the device (e.g., the patient is too young for the system), then the system automatically provides a warning and will not initiate care, but is still able to contact medical authorities. In one embodiment, the device is unable to be used on a particular patient, the device automatically displays pictorial instructions for how to ventilate the individual without the use of the device.

In one embodiment, the device does not include a confirmation screen wherein the user needs to confirm that quantities such as tidal volume, respiratory rate, etc. for the system are correct based on the input patient attributes (e.g., height, weight, gender, etc.). This is helpful, as it does not put the burden of understanding complex medical terminology on a potentially unsophisticated user or potentially confuse the user and prevent the device from being activated as quickly as is necessary to save a patient.

Figure 7:
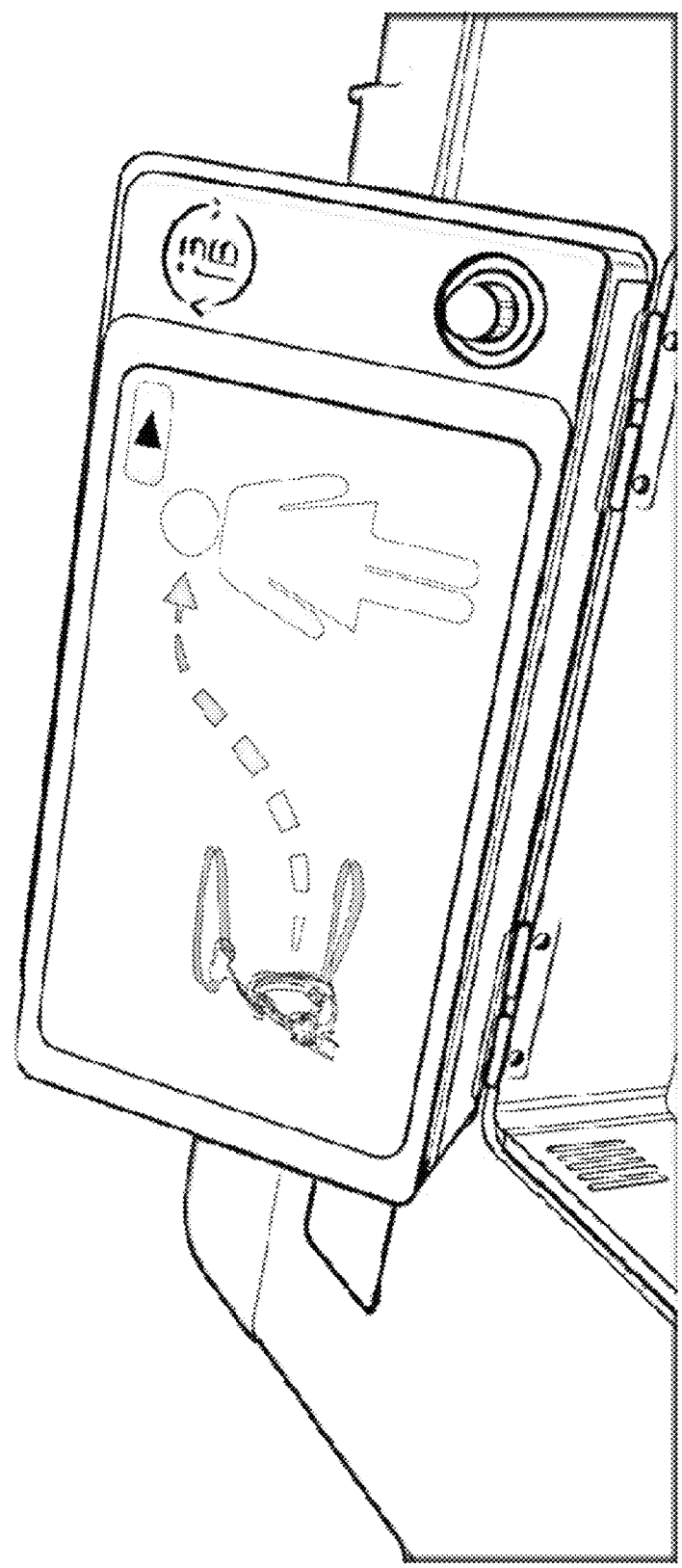
FIG. 7 is a perspective view of a display and input interface of a portable ventilator showing an instructions screen according to one embodiment of the present invention.

FIG. 7 is an illustrative instructions screen. The instructions are preferably pictographic and/or animated to provide clarity to even untrained or minimally trained users. While not expressly shown, it is understood that other screens are possible including output screens on the patient, alarm indicators, and other instructions if follow up actions are needed such as a mask needing adjustment to avoid a leak and so forth. In one embodiment, if the ventilator system receives input that the patient is also undergoing cardiac arrest, at least one instructions screen is generated with a pictorial graphic indicating where on the patient's chest to perform compressions. In one embodiment, ventilation system provides an indication of timing (e.g., a periodically flashing color, a metronome beat, etc.) for performing the compressions.

Figure 8:
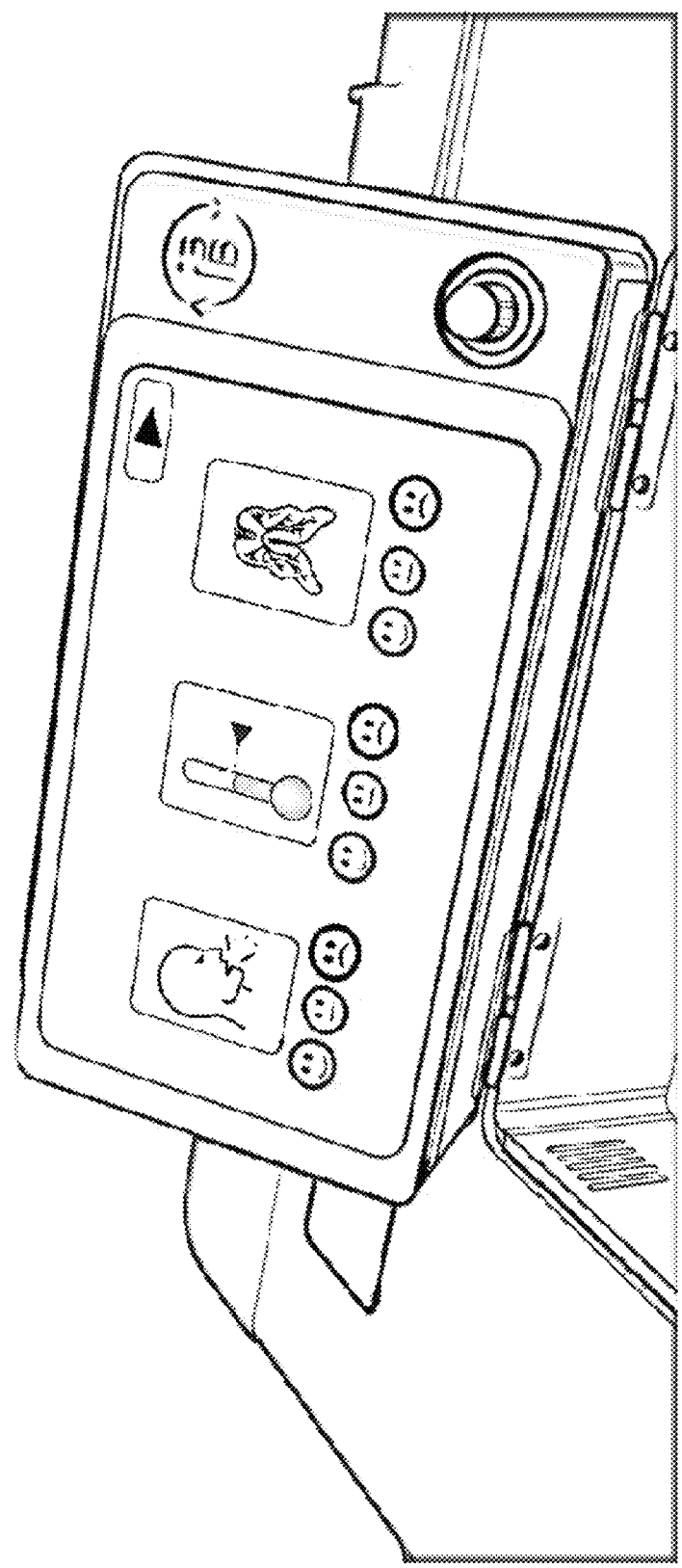
FIG. 8 is a perspective view of a display and input interface of a portable ventilator showing a patient conditions input interface according to one embodiment of the present invention.

FIG. 8 is an illustrative user interface screen for conditions of the patient. In one embodiment, the conditions include, for example, how well the patient is breathing, patient temperature, or other conditions (e.g., whether the patient is also having a heart attack). In one embodiment, each condition is symbolized by a pictorial graphic image in addition to or in lieu of text, allowing for easier use by operators who are literate in different languages.

Figure 9:
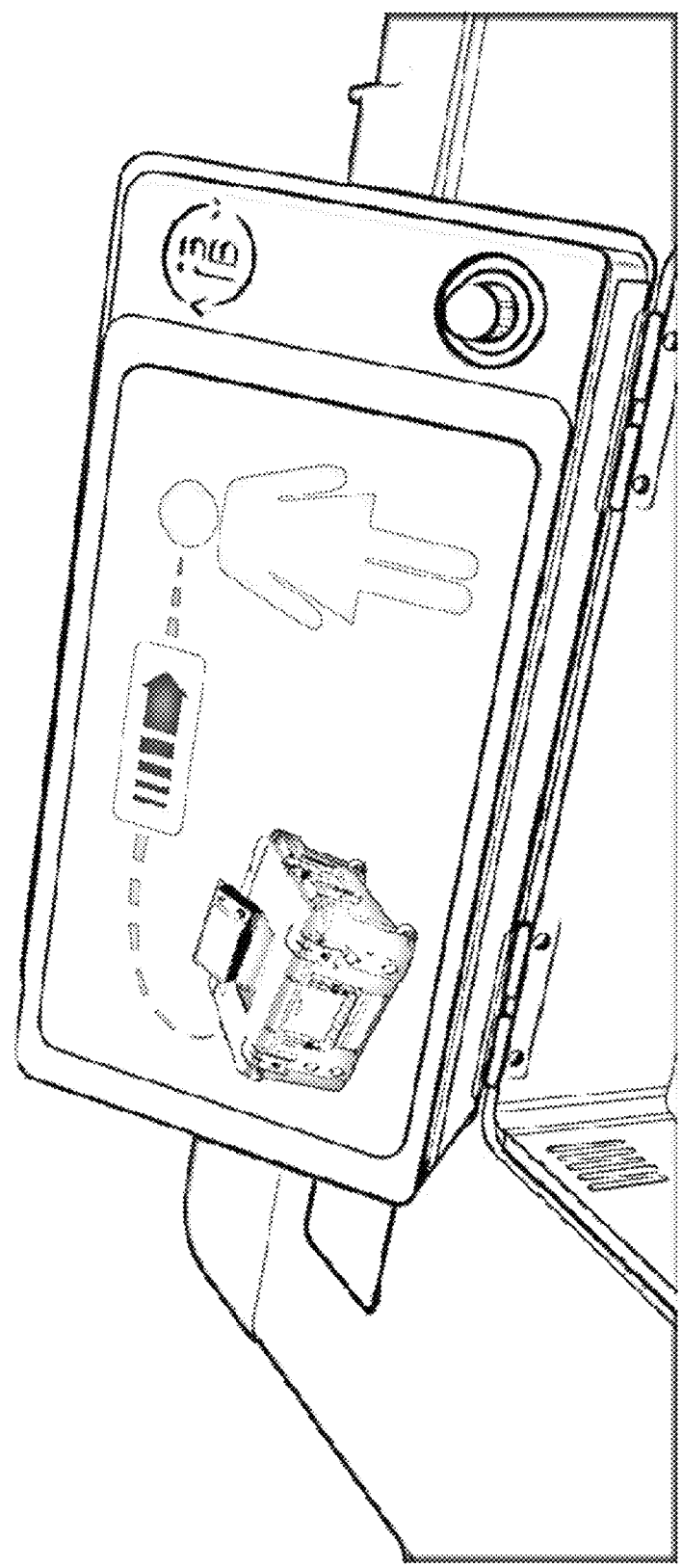
FIG. 9 is a perspective view of a display and input interface of a portable ventilator showing an activation screen according to one embodiment of the present invention.

FIG. 9 is an illustrative user interface screen for commencing operation. With the initial input, the ventilator commences operations of the respiration. The pictographic instructions assist in directing user actions. In one embodiment, voice instructions in an appropriate language are used.

In one embodiment, the ventilator system is operable to receive voice commands to provide the input characteristics for the patient (e.g., height, weight, sex, age, etc.). In one embodiment, the ventilator system is operable to prompt each step through auditory messages.

Figure 10:
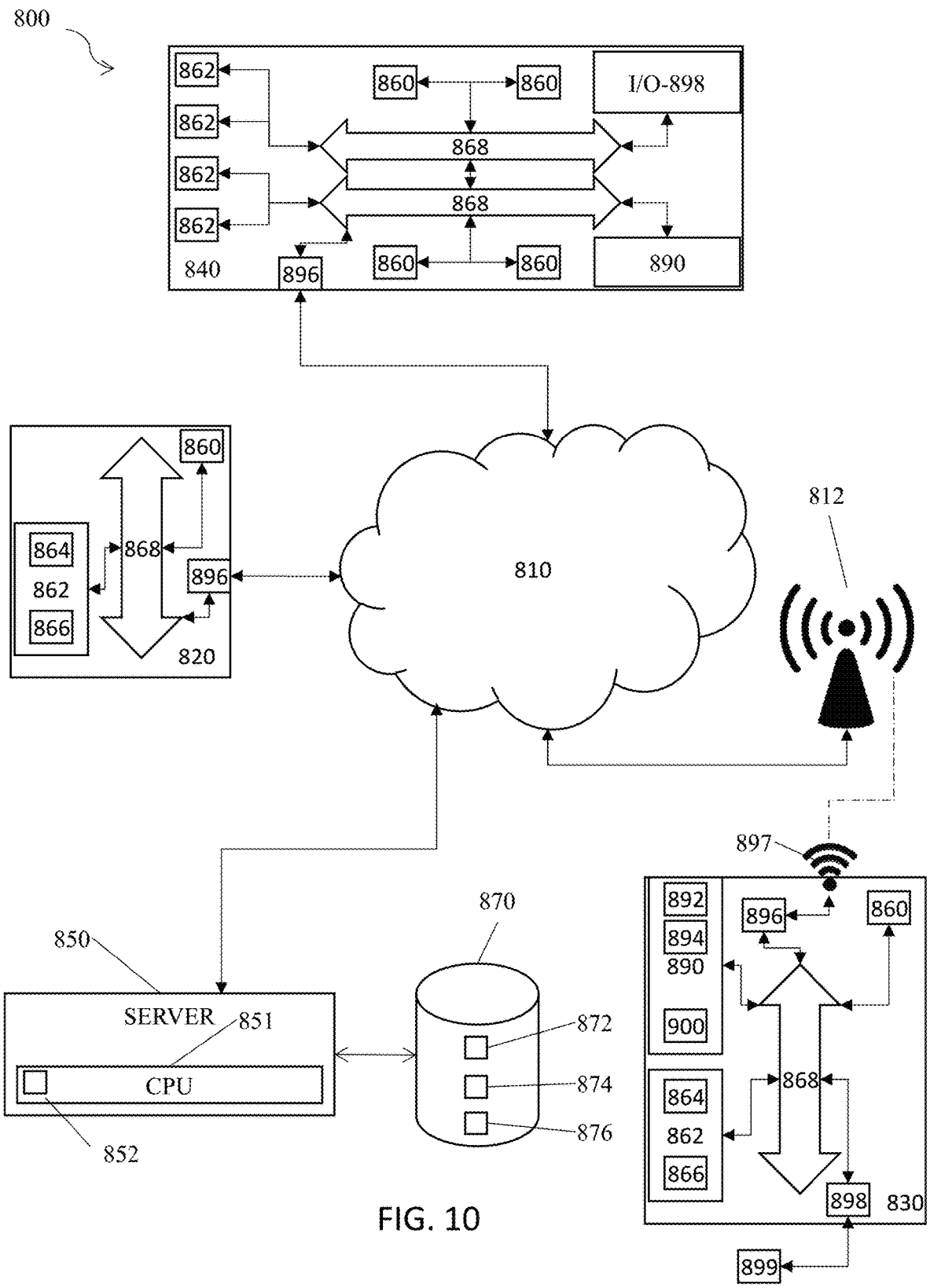
FIG. 10 is a schematic diagram of a system of the present invention.

FIG. 10 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, gaming controllers, joy sticks, touch pads, signal generation devices (e.g., speakers), augmented reality/virtual reality (AR/VR) devices (e.g., AR/VR headsets), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that perform calculations, process instructions for execution, and/or other manipulations of information.

In another implementation, shown as 840 in FIG. 10, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that stores the computer readable instructions and which are accessible by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 10, is operable to include other components that are not explicitly shown in FIG. 10, or is operable to utilize an architecture completely different than that shown in FIG. 10. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans are able to implement the described functionality in varying ways for each particular application (e.g., arranged in a different order or partitioned in a different way), but such implementation decisions should not be interpreted as causing a departure from the scope of the present invention.

It must be understood that the inventions disclosed and taught herein are susceptible to numerous and various modifications and alternative forms. The use of a singular term, such as, but not limited to, "a," is not intended as limiting of the number of items. Further, the various methods and embodiments of the system are able to be included in combination with each other to produce variations of the disclosed methods and embodiments. Discussion of singular elements are also inclusive of plural elements and vice-versa. References to at least one item include one or more items. Also, various aspects of the embodiments are used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The term "coupled," "coupling," "coupler," and like terms are used broadly herein and include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and are able to further include without limitation integrally forming one functional member with another in a unity fashion. The coupling is able to occur in any direction, including rotationally. The device or system is able to be used in a number of directions and orientations. The order that steps are able to occur in a variety of sequences unless otherwise specifically limited. The various steps described herein are combined with other steps, interlineated with the stated steps, and/or split into multiple steps. Some elements are nominated by a device name for simplicity and would be understood to include a system or a section, such as a controller encompasses a processor and a system of related components that are known to those with ordinary skill in the art and may not be specifically described. Various examples are provided in the description and figures that perform various functions and are non-limiting in shape, size, description, but serve as illustrative structures that are able to be varied as would be known to one with ordinary skill in the art given the teachings contained herein. As used herein, "patient" refers to a person in need of respirator assistance and is not restricted to a person under the care of a physician or medical center.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components are able to take on. All modifications and improvements have been deleted herein for the sake of conciseness and readability but are properly within the scope of the present invention.

The invention claimed is:

1. A portable emergency ventilator system, comprising:
   a controller;
   a mechanical ventilator with an inspiratory pathway and an exhalation pathway connected to tubing operable to supply air to at least one patient; and
   at least one geolocation sensor and a wireless module;
   wherein the controller is in communication with at least one user input device, including a display screen;

wherein the at least one user input device receives input values corresponding to a height, a weight, and/or a sex of the at least one patient;

wherein the received input values do not include tidal volume, positive end-expiratory pressure, respiratory rate, or inspiratory airflow of the at least one patient;

wherein the controller initiates operation of the mechanical ventilator and controls a pressure of air delivered by the mechanical ventilator to the at least one patient based on the received input values;

wherein the controller is operable to change operational parameters of the mechanical ventilator during operation based on physiological response from the at least one patient;

wherein the controller initiates operation of the mechanical ventilator in a first mode and later automatically changes operation of the mechanical ventilator to a second mode based on sensor data corresponding to the at least one patient;

wherein the first mode detects a number of attempted breaths from the at least one patient by detecting negative pressure measurements from one or more sensors;

wherein different modes of the mechanical ventilator differ in the support of spontaneous breaths;

wherein the display screen is operable to show instructions for connecting the mechanical ventilator to the at least one patient; and wherein the wireless module is configured to transmit geolocation data generated by the at least one geolocation sensor to an external medical facility, medical provider, and/or emergency service.

2. The system of claim 1, wherein the controller is connected to a memory and/or in communication with a database, and wherein the memory and/or the database include a plurality of data point correlations between a first group of quantities, including height, weight, and/or sex, and a second group of quantities, including tidal volume, positive end-expiratory pressure, respiratory rate, and/or inspiratory airflow.

3. The system of claim 2, wherein the controller automatically generates estimated values for the tidal volume, the positive end-expiratory pressure, the respiratory rate, and/or the inspiratory airflow of the at least one patient based on the input values and the plurality of data point correlations in the memory and/or the database, and wherein the controller controls the volume and/or the pressure of air delivered by the mechanical ventilator based on the estimated values.

4. The system of claim 1, further including at least one inspiratory pressure sensor configured to detect a pressure of air passing between the mechanical ventilator and the at least one patient.

5. The system of claim 4, wherein the controller receives data from the at least one inspiratory pressure sensor and changes parameters for operation of the mechanical ventilator based on the received data.

6. The system of claim 1, wherein the user input device receives the height and/or the weight via at least one interactive slider element.

7. The system of claim 1, wherein the second mode is able to be one of a plurality of modes, and wherein the plurality of modes include assist/control (A/C), synchronous intermittent mandatory ventilation (SIMV), continuous positive airway pressure (CPAP), pressure support ventilation (PSV), volume support (VS), control mode ventilation (CMV), airway pressure release ventilation (APRV), mandatory minute ventilation (MMV), inverse ratio ventilation (IRV), pressure-regulated volume control (PRVC), proportional assist ventilation (PAV), adaptive support ventilation (ASV), adaptive pressure control (APC), volume-assisted pressure support (VAPS), neurally adjusted ventilatory assist (NAVA), automatic tube compensation (ATC), and/or high frequency oscillatory ventilation (HFOV).

8. The system of claim 1, wherein the system is integrated with an automated external defibrillator (AED).

9. The system of claim 1, wherein the input values further include indications of a health status of the at least one patient, and wherein the health status of the at least one patient includes a body temperature and/or whether the at least one patient is in cardiac arrest.

10. A portable emergency ventilator system, comprising:
a casing containing a controller, at least one geolocation sensor, a wireless module, and a mechanical ventilator;

wherein the mechanical ventilator is connected to tubing operable to supply air to at least one patient;

wherein the controller is in communication with at least one user input device;

wherein the at least one user input device receives input values corresponding to a height, a weight, and/or a sex of the at least one patient;

wherein the controller initiates operation of the mechanical ventilator and controls pressure of air delivered by the mechanical ventilator to the at least one patient based on the received input values;

wherein the controller is operable to change operational parameters of the mechanical ventilator during operation based on physiological response from the at least one patient;

wherein the controller initiates operation of the mechanical ventilator in a first mode and later automatically changes operation of the mechanical ventilator to a second mode based on sensor data corresponding to the at least one patient;

wherein the first mode detects a number of attempted breaths from the at least one patient by detecting negative pressure measurements from one or more sensors;

wherein different modes of the mechanical ventilator differ in the support of spontaneous breaths;

wherein the casing includes at least one recession shaped to hold the tubing;

wherein the casing is attached to at least one flap, where the flap is configured to cover the recession in the casing in a closed position;

wherein the portable emergency ventilator system is configured to be mounted within a cabinet; and wherein the wireless module is configured to transmit geolocation data generated by the at least one geolocation sensor.

11. The system of claim 10, wherein the at least one flap is pivotably attached to the casing.

12. The system of claim 10, wherein the controller is connected to a memory and/or in communication with a database, and wherein the memory and/or the database include a plurality of data point correlations between a first group of quantities including height, weight, and/or sex and a second group of quantities, including tidal volume, positive end-expiratory pressure, respiratory rate, and/or inspiratory airflow.

13. The system of claim 12, wherein the controller automatically generates estimated values for the tidal volume, the positive end-expiratory pressure, the respiratory rate, and/or the inspiratory airflow of the at least one patient based on the input values and the plurality of data point correlations in the memory and/or the database, and wherein the controller controls the volume and/or the pressure of air delivered by the mechanical ventilator based on the estimated values.

14. The system of claim 10, wherein the input values further include indications of a health status of the at least one patient, and wherein the health status of the at least one patient includes a body temperature and/or whether the at least one patient is in cardiac arrest.

15. The system of claim 10, wherein the user input device receives the height and/or the weight via at least one interactive slider element.

16. The system of claim 10, wherein the second mode is able to be one of a plurality of modes, and wherein the plurality of modes include assist/control (A/C), synchronous intermittent mandatory ventilation (SIMV), continuous positive airway pressure (CPAP), pressure support ventilation (PSV), and/or volume support (VS).

17. A portable emergency ventilator system, comprising:
a controller;
a mechanical ventilator with an inspiratory pathway and an exhalation pathway connected to tubing operable to supply air to at least one patient; and
at least one geolocation sensor and a wireless module;
wherein the controller is in communication with at least one user input device, including a display screen;
wherein the at least one user input device receives input values corresponding to a height, a weight, and a sex of the at least one patient;
wherein the controller is connected to a memory and/or in communication with a database, and wherein the memory and/or the database include a plurality of data point correlations between a first group of quantities including height, weight, and/or sex and a second group of quantities, including tidal volume, positive end-expiratory pressure, respiratory rate, and/or inspiratory airflow;
wherein the controller automatically generates estimated values for the positive end-expiratory pressure, and/or the inspiratory airflow of the at least one patient based on the input values and the plurality of data point correlations in the memory and/or the database;
wherein the controller initiates operation of the mechanical ventilator and automatically controls a pressure of air delivered by the mechanical ventilator to the at least one patient based on the estimated values;
wherein the controller initiates operation of the mechanical ventilator in a first mode and later automatically changes operation of the mechanical ventilator to a second mode based on sensor data corresponding to the at least one patient;
wherein the first mode detects a number of attempted breaths from the at least one patient by detecting negative pressure measurements from one or more sensors;
wherein different modes of the mechanical ventilator differ in the support of spontaneous breaths;
wherein the display screen is operable to show instructions for connecting the mechanical ventilator to the at least one patient; and
wherein the wireless module is configured to transmit geolocation data generated by the at least one geolocation sensor.

18. The system of claim 17, wherein the input values further include indications of a health status of the at least one patient, and wherein the health status of the at least one patient includes a body temperature and/or whether the at least one patient is in cardiac arrest.

19. The system of claim 17, wherein the user input device receives the height and/or the weight via at least one interactive slider element.

20. The system of claim 17, wherein the second mode is able to be one of a plurality of modes, and wherein the plurality of modes include assist/control (A/C), synchronous intermittent mandatory ventilation (SIMV), continuous positive airway pressure (CPAP), pressure support ventilation (PSV), and/or volume support (VS).

* * * * *